United States Patent
Rast et al.

(10) Patent No.: US 12,337,020 B2
(45) Date of Patent: Jun. 24, 2025

(54) BACTERIOPHAGE COMPOSITIONS

(71) Applicants: TAKEDA GMBH, Constance (DE);
TAKEDA PHARMACEUTICAL COMPANY LTD., Osaka (JP)

(72) Inventors: Markus Rast, Singen (DE); Sergio Rodriguez-Morillas, Basel (CN); Tomomine Iida, Osaka (JP)

(73) Assignee: TAKEDA PHARMACEUTICAL COMPANY LTD., Osaka (JP)

( * ) Notice: Subject to any disclaimer, the term of this patent is extended or adjusted under 35 U.S.C. 154(b) by 993 days.

(21) Appl. No.: 17/047,611

(22) PCT Filed: Apr. 17, 2019

(86) PCT No.: PCT/EP2019/060027
§ 371 (c)(1),
(2) Date: Oct. 14, 2020

(87) PCT Pub. No.: WO2019/202051
PCT Pub. Date: Oct. 24, 2019

(65) Prior Publication Data
US 2021/0121510 A1    Apr. 29, 2021

(30) Foreign Application Priority Data

Apr. 18, 2018 (EP) .................................. 18167994

(51) Int. Cl.
*A61K 35/76* (2015.01)
*A61K 9/16* (2006.01)

(52) U.S. Cl.
CPC ............ *A61K 35/76* (2013.01); *A61K 9/1623* (2013.01); *A61K 9/1652* (2013.01); *C12N 2795/10132* (2013.01); *C12N 2795/10232* (2013.01); *C12N 2795/10332* (2013.01)

(58) Field of Classification Search
None
See application file for complete search history.

(56) References Cited

U.S. PATENT DOCUMENTS

| | | | |
|---|---|---|---|
| 8,012,507 B2 | 9/2011 | Troung-Le et al. | |
| 2008/0118468 A1* | 5/2008 | Sulakvelidze | A61K 39/0275 435/235.1 |
| 2009/0093041 A1 | 4/2009 | Walbeck | |

FOREIGN PATENT DOCUMENTS

| | | |
|---|---|---|
| CN | 105950475 A | 9/2016 |
| CN | 107574155 A | 1/2018 |
| JP | 2006-512102 A | 4/2006 |
| WO | 2016/118738 A1 | 7/2016 |

OTHER PUBLICATIONS

Saboo, et al., "Optimized Formulation of a Thermostable Spray-Dried Virus-Like Particle Vaccine against Human Papillomavirus", Molecular Pharmaceutics, vol. 13, No. 5, May 2016.
Vandenheuvel, et al., "Feasibility of spray drying bacteriophages into respirable powsers to combat pulmonary bacterial infections", European Journal of Pharmaceutics and Biopharmaceutics, vol. 84, No. 3, Jan. 2013.
Malik, et al., "Formulation, stabilisation and encapsulation of bacteriophage for phage therapy", Advances in Colloid and Interface Science, vol. 249, May 2017.
Bodier-Montagutelli, et al., "Inhaled phage therapy: a promising and challenging approach to treat bacterial respiratory infections", Expert Opinion on a Drug Delivery, vol. 14, No. 8, Nov. 2016.
Merabishvili, et al., "Stability of *Staphylococcus aureus* Phage ISP after Freeze-Frying (Lyophilization)", PLOS ONE, vol. 8, No. 7, Jul. 2013.
Leclair, et al., "Evaluation of excipients for enhanced thermal stabilization of a human type 5 adenoviral vector through spray drying", International Journal of Pharmaceutics, vol. 506, No. 1, Apr. 2016.
Leclair, et al., Optimization of Spray Drying Conditions for Yield, Particle Size and Biological Activity of Thermally Stable Viral Vectors, Pharmaceutical Research, vol. 33, No. 11, Jul. 2016.
Engel, et al., "The preservation of mycobacteriophages by means of freeze drying", The American Review of Respiratory Disease, American Thoracic Society, vol. 109, No. 5, Apr. 1974.
Gonzalez-Menendez, et al., "Comparative analysis of different preservation techniques for the storage of *Staphylococcus* phages aimed for the industrial development of phage-based antimicrobial products", PLOS ONE, vol. 13, No. 10, Oct. 2018.
Anany, et al., Biocontrol of Listeria monocytogenes and *Escherichia coli* O157:H7 in Meat by Using Phages Immobilized on Modified Cellulose Membranes, Applied and Environmental Microbiology, vol. 77, No. 18, Sep. 2011.
Tang, et al., "Whey protein improves survival and release characteristics of bacteriophage Felix 01 encapsulated in alginate microsphers", Food Research International, vol. 52, No. 2, Dec. 2012.
Ma, et al., "Enhanced alginate microspheres as means of oral delivery of bacteriophage for reducing intestinal carriage", Food Hydrocolloids, vol. 26, No. 2, Nov. 2010.
Leung, et al., "Production of Inhalation Phage Powders Using Spray Freeze Drying and Spray Drying Techniques for Treatment of Respiratory Infections", Pharmaceutical Research, vol. 33, No. 6, Feb. 2016.

* cited by examiner

*Primary Examiner* — Stacy B Chen
(74) *Attorney, Agent, or Firm* — Nath, Goldberg & Meyer; Joshua B. Goldberg

(57) ABSTRACT

The present invention relates to a bacteriophage composition comprising at least one bacteriophage species, at least one α-linked polymeric glucose and at least one polyol. In certain embodiments, the α-linked polymeric glucose has a mean molecular weight of greater than 10 kDa.

20 Claims, 2 Drawing Sheets

BACTERIOPHAGE COMPOSITIONS

This is a National Phase Application filed under 35 U.S.C. 371 as a national stage of PCT/EP2019/060027, filed Apr. 17, 2019, an application claiming the benefit of European Application No. 18167994.5, filed Apr. 18, 2018 the content of each of which is hereby incorporated by reference in its entirety.

TECHNICAL FIELD OF THE INVENTION

The present invention relates to a pharmaceutical bacteriophage composition and processes of manufacture, method of treatment therewith and uses thereof.

BACKGROUND OF THE INVENTION

Bacteriophages (in short phages) are naturally occurring viruses specific for particular types of bacteria. Bacterial infections can be controlled in humans, animals and plants by application of phages, which attack and kill these bacteria.

Since the 1940s, antibiotics have saved numerous lives with respect to bacterial infections, but with the increased emergence of bacterial resistance against most antibiotics, the search for valid alternative methods of treating bacterial infections has gained both scientific and medical attention. A further disadvantage of antibiotic treatment is the unspecific eradication of bacteria after oral administration in the gastrointestinal tract. Microbiome research has shown that the growing numbers of patients suffering from ulcerative colitis and Crohn's disease are related to antibiotic treatment. Therefore, therapies that are more specific are needed.

Phage therapy could be useful in the treatment of gastrointestinal bacterial infections and disorders by specifically targeting pathogenic bacteria, but not eradicating bacteria, which are useful in digestion.

Bacteriophages show high bacterial strain specificity. As the bacterial components of a disease may differ from patient to patient, it is often necessary to use cocktail treatments for the same infection or disease for a high chance of success Phage therapy has been used in Eastern Europe and the former Soviet Union, with its use being particularly widespread in Georgia.

Bacteriophage represent extremely complicated therapeutics since they are comprised of DNA, or RNA and proteins. Frequently, bacteriophages contain elaborate receptor-binding tail structures that are particularly sensitive to breakage. A severe limitation of the ability to exploit the therapeutic potential of bacteriophages is the sensitivity of bacteriophages to low pH, proteolytic degradation and denaturation due to drying, and the lack of suitable methods for preparing economical and effective solid dosage forms.

Typically, phage preparations used therapeutically are produced in liquid formulation. It is, however, often desirable to supply a dry phage product, as production of dry forms of bacteriophage compositions can help to increase the stability of the bacteriophage when stored at room temperature and at high humidity levels. In addition, having access to a dry phage product allows the development of solid oral dosage forms.

There exist certain different drying methods in the art. Lyophilisation is a known drying method for sensitive materials. Lyophilisation, however, is a rather slow and costly drying technology. A more convenient and cost effective method is spray drying. In spray drying a liquid feed is atomized into very small droplets that are dried in a hot air stream. The powder is then collected e.g. in a cyclone. Spray drying has several main advantages compared to lyophilisation, these are:
- it is a rather simple and cost efficient technology,
- it is a fast process which in principle can be run continuously,
- it results in the formation of a fine powder instead of a solid cake, which can be advantageous for a later resuspension of the product for administration in liquid form.

However, spray drying includes elevated temperatures and sheer stress, which can be detrimental to complex and large structures like bacteriophages.

Thus, there remains a need in the art for methods of stabilizing bacteriophage compositions under a wide range of process conditions and in particular under the conditions of spray drying.

OBJECTS AND SUMMARY OF THE INVENTION

It is an object of the present invention to provide compositions, in particular dry compositions, containing bacteriophage species, in particular compositions containing mixtures of bacteriophage species.

It is a further object of the present invention to provide bacteriophage compositions, in particular compositions comprising mixtures of bacteriophage species, suitable for spray-drying processes, and the corresponding dry compositions and drying techniques.

The above objects are achieved by embodiments of the present invention as described and claimed herein.

The present invention is, therefore, directed to a bacteriophage composition comprising:
- at least one bacteriophage species,
- at least one α-linked polymeric glucose
- at least one polyol,
- and optionally other ingredients selected from the group of buffer salts, electrolytes, surfactants and the like.

The present invention is also directed to the use of α-linked polymeric glucose and at least one polyol, for the stabilization of bacteriophage species during spray drying.

The present invention is further directed to the process of preparing a dried bacteriophage composition comprising at least step 1 and step 2, involving preparing in step 1 a composition in an evaporable liquid comprising:
- at least one bacteriophage species,
- at least one α-linked polymeric glucose,
- at least one polyol,
- and optionally other ingredients selected from the group of buffer salts, electrolytes, surfactants and the like,
and
- spray drying said composition from step 1 in step 2 to obtain a dry bacteriophage composition.

The present invention is also directed to a bacteriophage composition in accordance with the invention for use in the treatment of a bacterial infection.

The present invention is also directed to the use of a bacteriophage composition in accordance with the invention for the manufacture of a medicament for the treatment of a bacterial infection.

The present invention is further directed to a method of treating a bacterial infection comprising administering to an animal or human patient in need of such a treatment a unit dose of the dry bacteriophage composition according to the invention.

DEFINITIONS

Figure 1:
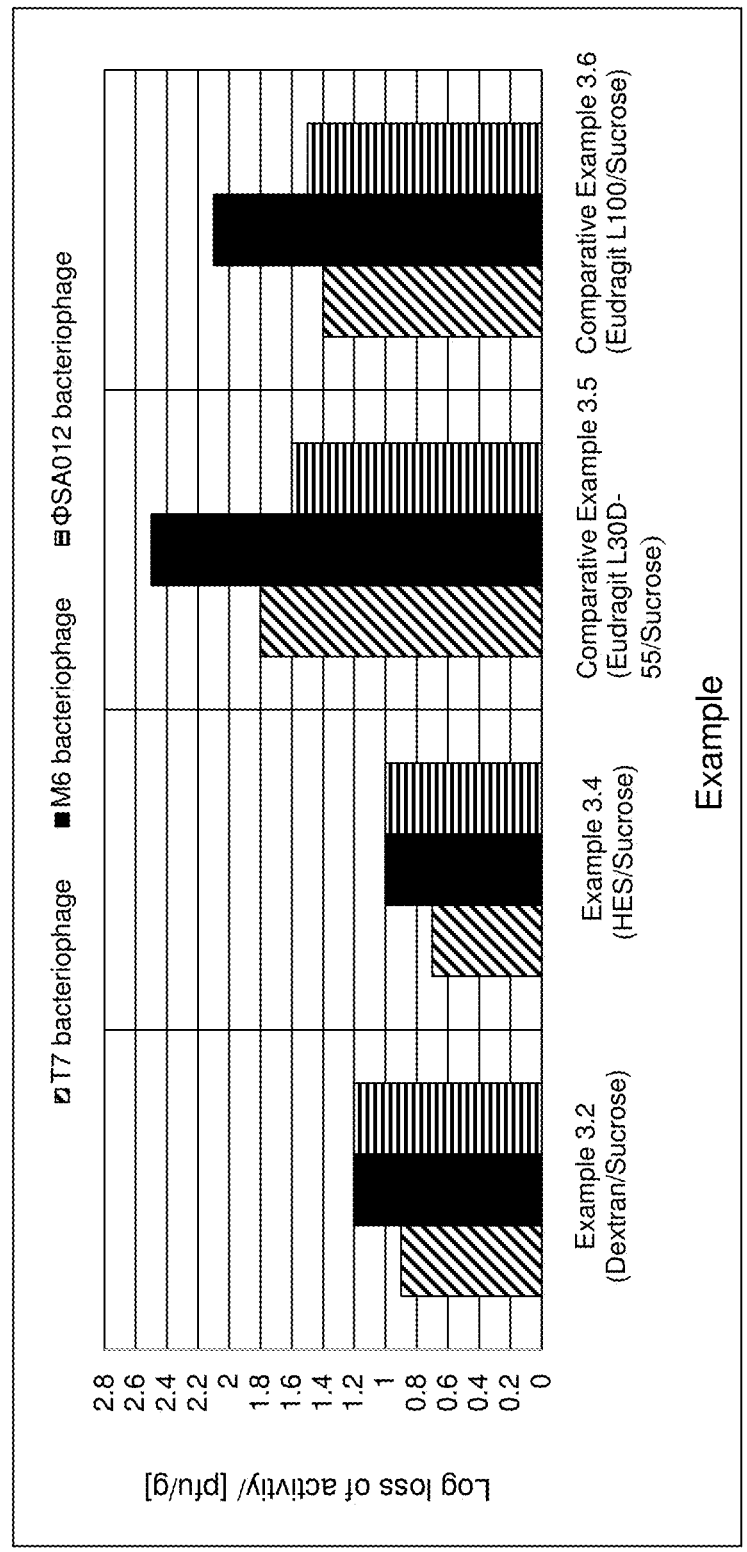
FIG. 1 is a graph showing the log loss of activity after spray drying for each of the bacteriophage species in compositions containing more than 1 bacteriophage species according to Example 3 (3.2, 3.4 and Comparative Examples 3.5 and 3.6).

Unless defined otherwise, all technical and scientific terms used herein have the same meaning as commonly understood by one of ordinary skill in the art to which the invention pertains. Although, any methods and materials similar or equivalent to those described herein can be used in practice for testing of the present invention, the preferred materials and methods are described herein. In describing and claiming the present invention, the following terminology will be used in accordance with the definitions set out below. Unless clearly indicated otherwise, use of the terms "a," "an," and the like refers to one or more.

"Resuspension" (or "resuspending") or "reconstitution" (or "reconstituting") refers to the contacting of the spray dried powder with a pharmaceutically acceptable liquid e.g. (preferably sterile) water or a (preferably sterile) customary buffer or a saline solution such that the powder is converted to either a suspension or a solution which can be administered to a patient, e.g. orally or by injection.

"Dry composition" or "composition in dry form" refers to a solid material with a residual water content of less than about 10%. Dried compositions are preferably dried to residual liquid (water) contents of 8% or less, 5% or less, or preferably from about 0.1% to about 5%. Preferably, the residual water content is determined in accordance with the Karl Fisher Titration method as disclosed in the test methods section.

The term "oligomer" is defined for the purposes of the present invention to refer to an oligomer with an average of from 3 to 5 repeating units, or from 3 to 10 repeating units, or from 3 to 15 repeating units, or from 3 to 20 repeating units e.g. maltodextrin (maltodextrin is a typical glucose oligomer obtained by partially hydrolysing starch, a typical glucose polymer). Maltodextrins are classified by DE (dextrose equivalent) and have a DE between 3 and 20, while pure glucose has a DE of 100 and typical starch (polymeric glucose) has a DE of about 0. DE can be determined by the method according to the European Pharmacopoeia (European Pharmacopoeia (Ph. Eur.) $9^{th}$ Edition (9.0)) provided for maltodextrin. The average number of repeating units may be determined by dividing the mean molecular weight ($M_w$) by the molecular weight of the repeating unit. The mean molecular weight ($M_w$) of the oligomer may be determined by the method provided by the European Pharmacopoeia (European Pharmacopoeia (Ph. Eur.) $9^{th}$ Edition (9.0)). The mean molecular weight may in particular be determined by using size exclusion chromatography as described in the test methods section (2.2.30).

The term "α-linked polymeric glucose" is defined for the purposes of the present invention to refer to polysaccharides composed entirely of glucose, linked together by alpha glycosidic bonds. This definition encompasses both linear and branched chain molecules. Within the meaning of this invention α-linked polymeric glucoses have an average number of repeating units of more than about 20; consequently, oligomers as defined above are not included in this definition, in particular maltodextrins. Examples of α-linked polyglucoses, within the meaning of this invention, include starch, dextran and glycogen. The average number of repeating units may be determined by the mean molecular weight ($M_w$, e.g. the weight average molecular weight) which may be determined by the method provided by the European Pharmacopoeia (European Pharmacopoeia (Ph. Eur.) $9^{th}$ Edition (9.0)). The mean molecular weight may in particular be determined by using size exclusion chromatography as described in the test methods section. For HES and dextran specific methods are provided in the respective test methods and monograph sections.

The term "starch" is defined for purposes of the present invention to refer to both naturally occurring starches; but also chemically modified starch derived materials, such as hydroxyl ethyl starch. Characterisation of certain starches such as e.g. HES can be found in the European Pharmacopoeia (European Pharmacopoeia (Ph. Eur.) $9^{th}$ Edition (9.0)).

The term "polyol" is defined for purposes of the present invention to refer to a substance with multiple hydroxyl groups, and includes sugars (reducing and non-reducing sugars), sugar alcohols and sugar acids. Polyols as defined herein have a molecular weight which is less than about 600 Da (e.g. in the range from about 120 to about 400 Da).

The term "T7" is defined for purposes of the present invention to refer to *Escherichia coli* phage T7 (Podoviridae).

The term "M6" is defined for purposes of the present invention to refer to *Pseudomonas aeruginosa* phage M6 (Siphoviridae).

The term "φSA012" is defined for purposes of the present invention to refer to *Staphylococcus aureus* phage φSA012 (Myoviridae).

Bacteriophages are viruses that are able to infect bacteria and archaea and replicate therein. Bacteriophages are composed of proteins that encapsulate a DNA or RNA genome. The term "bacteriophage species" refers to a monophyletic group of bacteriophages whose properties can be distinguished from those of other species by multiple criteria. Examples of bacteriophage species include e.g. T7, M6 and φSA012. It is understood that the bacteriophage species according to the present invention comprise "live" bacteriophages for which a pfu titer can be determined, "live" bacteriophages do not include e.g. virus like particles (VLPs).

The term "pfu" is defined for purposes of the present invention to refer to plaque forming units determined through a plaque assay. Within the meaning of this invention the activity is defined as the number of plaque forming units (pfu) measured in a plaque assay per gram of dried composition or per millilitre of composition.

If not indicated otherwise "%" refers to weight-%.

The term "patient" used herein refers to a subject, a human or an animal, that has presented a clinical manifestation of a particular symptom or symptoms suggesting the need for treatment and that is treated preventatively or prophylactically for a condition, or that has been diagnosed with a condition to be treated.

The term "about" is for purposes of the present invention understood to mean that there can be variation in the respective value or range (such as temperature, percentage, molecular weight etc.) that can be up to 5%, up to 10%, up to 15% and up to and including 20% of the given value.

The formulation of the invention referred to herein as the "composition" may preferably be in various physical states such as liquid, frozen, lyophilized, spray-dried and reconstituted formulations.

The term "capsule" is defined for purposes of the present invention to refer to a protective case, which can be used to encase a "unit dosage" of medication.

The term "yield" is defined for purposes of the present invention to refer to the mass of product obtained after spray drying. The term "percentage yield" or "% yield" is defined for the purposes of the present invention as:

$$\% \text{ yield} = \frac{\text{mass of product obtained after spray drying}}{\text{mass of anhydrous excipients added to the liquid spray drying feed}} \times 100$$

The terms "lyophilized" or "freeze-dried" are defined for purposes of the present invention to refer to a substance obtained and/or obtainable from a drying procedure in which the material to be dried is first frozen followed by the removal of the ice or frozen solvent by sublimation under vacuum.

The term "spray-dried" is defined for purposes of the present invention to refer to a substance obtained and/or obtainable from a drying procedure in which the material to be dried is sprayed through a nozzle and dried.

The term "contact temperature" is defined for the purposes of the present invention as the temperature of any surface (e.g. nozzle) or gas, which the liquid feedstock in a drying process comes into contact with during the course of the drying process.

DETAILED DESCRIPTION

Bacteriophage Species

The bacteriophage compositions according to the invention comprise at least one bacteriophage species, such as e.g. T7, M6 or φSA012, or two different bacteriophage species such as e.g. T7 and M6 or φSA012, or at least 3 different bacteriophage species, such as e.g. T7, M6 and φSA012.

At least one of the bacteriophage species may be selected from the group of e.g. Caudovirales. The bacteriophage species may be selected from the sub-groups of Myoviridae, Podoviridae, Siphoviridae, Microviridae, Leviviridae, Inoviridae or mixtures thereof, preferably from the sub-groups of Myoviridae, Podoviridae, Siphoviridae or mixtures thereof. The bacteriophage species may have a prolate shaped head or an isometric shaped head.

In certain embodiments, at least one of the bacteriophage species is effective against gram-positive bacteria, such as *Staphylococcus aureus* for example *Straphylococcus aureus* phage φSA012. In certain embodiments, one of the bacteriophage species is effective against gram-negative bacteria, such as *Escherichia coli* and *Pseudomonas aeruginosa*. For example the following bacteriophage species *Escherichia coli* phage T7 and *Pseudomonas aeruginosa* Phage M6.

The species mentioned above are to be understood as model bacteriophage species and the invention may be applied to other bacteriophage species with similar properties.

Composition

The present invention is directed to bacteriophage compositions comprising:

at least one bacteriophage species, and
at least one α-linked polymeric glucose,
at least one polyol,
and optionally other ingredients selected from the group of buffer salts, electrolytes and surfactants.

In certain embodiments, the α-linked polymeric glucose has a mean molecular weight ($M_w$) of from about 5 kDa to e.g. about 1000 kDa, of from about 10 kDa to e.g. about 1000 kDa, or from about 30 kDa to e.g. about 1000 kDa, or from about 40 kDa to e.g. about 1000 kDa, or from about 100 kDa to e.g. about 1000 kDa, or from about 150 kDa to e.g. about 1000 kDa, or from about 150 kDa to e.g. about 800 kDa.

In certain embodiments, the α-linked polymeric glucose is selected from the group of starches or modified starches. In certain such embodiments the α-linked polymeric glucose may be selected from the group of starches, hydroxyalkyl starches, such as hydroxyethyl starch, dextrans (such as dextran 40), amyloses and glycogens. According to preferred embodiments the α-linked polymeric glucose is selected from the group of hydroxyalkyl starches (such as hydroxyethyl starch 200/0.5 with a mean molecular weight of 200 kDa) or dextrans (such as dextran 40 with a mean molecular weight of 40 kDa).

The bacteriophage composition according to the present invention further comprises at least one polyol. Polyol compounds are believed to further stabilize the composition during drying. In certain embodiments, the polyol is selected from the group of saccharides, disaccharides (such as sucrose and trehalose) or sugar alcohols (such as sorbitol). Preferred embodiments include sucrose and sorbitol. In the most preferred embodiment, the polyol is sucrose.

In certain preferred embodiments the α-linked polymeric glucose included in the composition is hydroxyethyl starch and the polyol is sucrose.

In certain embodiments, the bacteriophage composition contains an α-linked polymeric glucose and a polyol, wherein the weight ratio of α-linked polymeric glucose to polyol is from about 9:1 to about 1:9, more preferably from about 9:2 to about 1:9, more preferably from about 6:2 to about 2:8 and most preferably about 4:6.

The bacteriophage composition may further comprise at least one buffer system, including but not limited to Tris-HCl, phosphate or histidine buffers. The concentration of the buffer salt may range from 1 mM to 1 M, preferably 1 mM to 200 mM, more preferably 3 mM to 50 mM and most preferably 3 mM to 25 mM, for example about 5 mM or about 20 mM.

In certain embodiments, the bacteriophage composition further comprises at least one electrolyte. For example inorganic salts (such as magnesium sulfate), amino acids (such as L- and D-Leucine). Additionally, the bacteriophage composition may contain surfactants such as Polysorbate 20 and Poloxamer 188.

Liquid Compositions

In one aspect the bacteriophage composition as described above is in the form of a liquid composition, such as an aqueous composition. Liquid compositions are used as compositions subjected to drying, but liquid compositions may also be used as reconstituted liquid compositions obtained from dispersing/dissolving the dry composition in a solvent.

In certain such embodiments, the pH of the liquid composition is from about 5 to about 10, such as about 5.5, or about 6.0, or about 6.5, or about 7.0, or about 7.5, or about 8.0, or about 8.5, or about 9.0 or about 9.5.

In certain embodiments, the activity of at least one bacteriophage species in the liquid composition is from about $1\times10^6$ (pfu/mL) to about $1\times10^{25}$ (pfu/mL), or from about $1\times10^8$ (pfu/mL) to about $1\times10^{25}$ (pfu/mL), or from about $1\times10^9$ (pfu/mL) to about $1\times10^{20}$ (pfu/mL). According to certain embodiments the compositions comprises 2 or more bacteriophage species, such as T7, M6 and φSA012. In certain such embodiments, the activity of at least two or at least three bacteriophage species in the liquid composition are from about $1\times10^6$ (pfu/mL) to about $1\times10^{25}$ (pfu/mL), or from about $1\times10^8$ (pfu/mL) to about $1\times10^{25}$ (pfu/mL), or from about $1\times10^9$ (pfu/mL) to about $1\times10^{20}$ (pfu/mL).

In certain embodiments, the liquid bacteriophage composition has a solids content of 1% w/w to 20% w/w or 2% w/w to 10% w/w or 3% w/w to 7% w/w.

In certain embodiments, the liquid bacteriophage composition contains a total mass of α-linked polymeric glucose from about 2% w/w to about 20% w/w of the total weight of the liquid composition, or from about 2% w/w to about 10% w/w, or from about 2% w/w to about 8% w/w.

In certain embodiments, the liquid bacteriophage composition contains a total mass of polyol from about 0.5% w/w to about 10% w/w of the total weight of the liquid composition, or from about 0.5% w/w to about 5% w/w of the total weight of the liquid composition, or from about 1% w/w to about 3% w/w of the total weight of the liquid composition.

Such liquid compositions may be subject to drying to obtain the dry composition. Such liquid compositions may also be formed from the dry composition as a reconstituted liquid composition.

In certain specific embodiments, the liquid bacteriophage composition comprises:
from about 3 mM to 10 mM Tris-HCl
from about 1% w/w to about 3% w/w of the liquid composition of hydroxyethyl starch
from about 2% w/w to about 4% w/w of the liquid composition of sucrose
from about 0.05% w/w to about 0.2% w/w of the liquid composition of leucine, and
wherein the composition
has a pH of about 7, and
wherein all the bacteriophage species have an activity of $1\times10^7$ (pfu/mL) to $1\times10^{20}$ (pfu/mL).

Dry Compositions

According to a further aspect of the invention the bacteriophage composition is in the form of a dry composition. Such dry compositions may be obtained by spray drying liquid bacteriophage compositions as described above, such as aqueous bacteriophage compositions. Alternatively, drying can be accomplished by other drying methods such as lyophilisation. The dry composition can be stored and used for solid dosage forms, such as solid oral dosage forms.

The dry bacteriophage composition has a liquid/water content of less than 10% w/w, or less than 8% w/w, or less than 5% w/w, or less than 4% w/w. The liquid/water content in certain embodiments ranges from 0.1% w/w to 10% w/w or 0.1% w/w to 8% w/w or 0.1% w/w to 5% w/w or 0.1% w/w to 4% w/w.

In certain such embodiments, the dry particles of the bacteriophage composition (determined by using a laser diffraction method with a Malvern Mastersizer 2000) are between 3 μm and 150 μm in mean diameter, or between 3 μm and 10 μm in mean diameter and or between 80 μm and 120 μm in mean diameter.

In certain embodiments, the dry bacteriophage composition is obtained by spray drying a liquid composition or by lyophilisation of a liquid composition.

In certain embodiments, the activity of at least one of the bacteriophage species in the dry bacteriophage composition is at least $1\times10^6$ (pfu/g) and optionally up to a maximum of $1\times10^{25}$ (pfu/g) per gram of dried composition, preferably at least $1\times10^8$ (pfu/g) and optionally up to a maximum of $1\times10^{25}$ (pfu/g) per gram of dried composition, or more preferably at least $1\times10^1$ (pfu/g) and optionally up to a maximum of $1\times10^{20}$ (pfu/g) per gram of dried composition. According to certain embodiments the compositions comprises 2 or more bacteriophage species, such as e.g. T7, M6 and φSA012. In such embodiments the activity of at least two or at least three of the bacteriophage species in the bacteriophage composition is at least $1\times10^6$ (pfu/g) and optionally up to a maximum of $1\times10^{25}$ (pfu/g) per gram of dried composition, preferably at least $1\times10^8$ (pfu/g) and optionally up to a maximum of $1\times10^{25}$ (pfu/g) per gram of dried composition or more preferably at least $1\times10^9$ (pfu/g) and optionally up to a maximum of $1\times10^{20}$ (pfu/g) per gram of dried composition.

Solid (Oral) Dosage Form

In certain embodiments, the bacteriophage composition is provided in a capsule, which may be an enteric-coated capsule.

In certain embodiments, the bacteriophage composition is provided in a tablet, which may be an enteric-coated tablet.

Method of Treatment/Medical Uses

In certain embodiments, the invention is directed to a method of treating a bacterial infection comprising administering to an animal or human patient in need of such a treatment a unit dose of the dry bacteriophage composition as described above, such as in the form of a capsule or tablet.

In certain embodiments, the invention is used for a method of treating bacterial infections in plants.

In certain embodiments, the invention is directed to a dry bacteriophage composition, such as in the form of a capsule or tablet for used in a method of treating a bacterial infection in an animal or human patient in need of such a treatment.

In certain embodiments, the invention is directed to a use of a dry bacteriophage composition, such as in the form of a capsule or tablet, in the manufacture of a medicament for treating a bacterial infection in an animal or human patient in need of such a treatment.

Process of Preparation

The present invention is also directed to a process of preparing a dried bacteriophage composition, which comprises at least step 1 and step 2, involving preparing in step 1 a composition in an evaporable liquid comprising:
at least one bacteriophage species,
at least one α-linked polymeric glucose,
at least one polyol,
and optionally other ingredients selected from the group of buffer salts, electrolytes, surfactants and the like, and
spray drying said liquid composition from step 1 in step 2 to obtain a dry bacteriophage composition.

Figure 2:
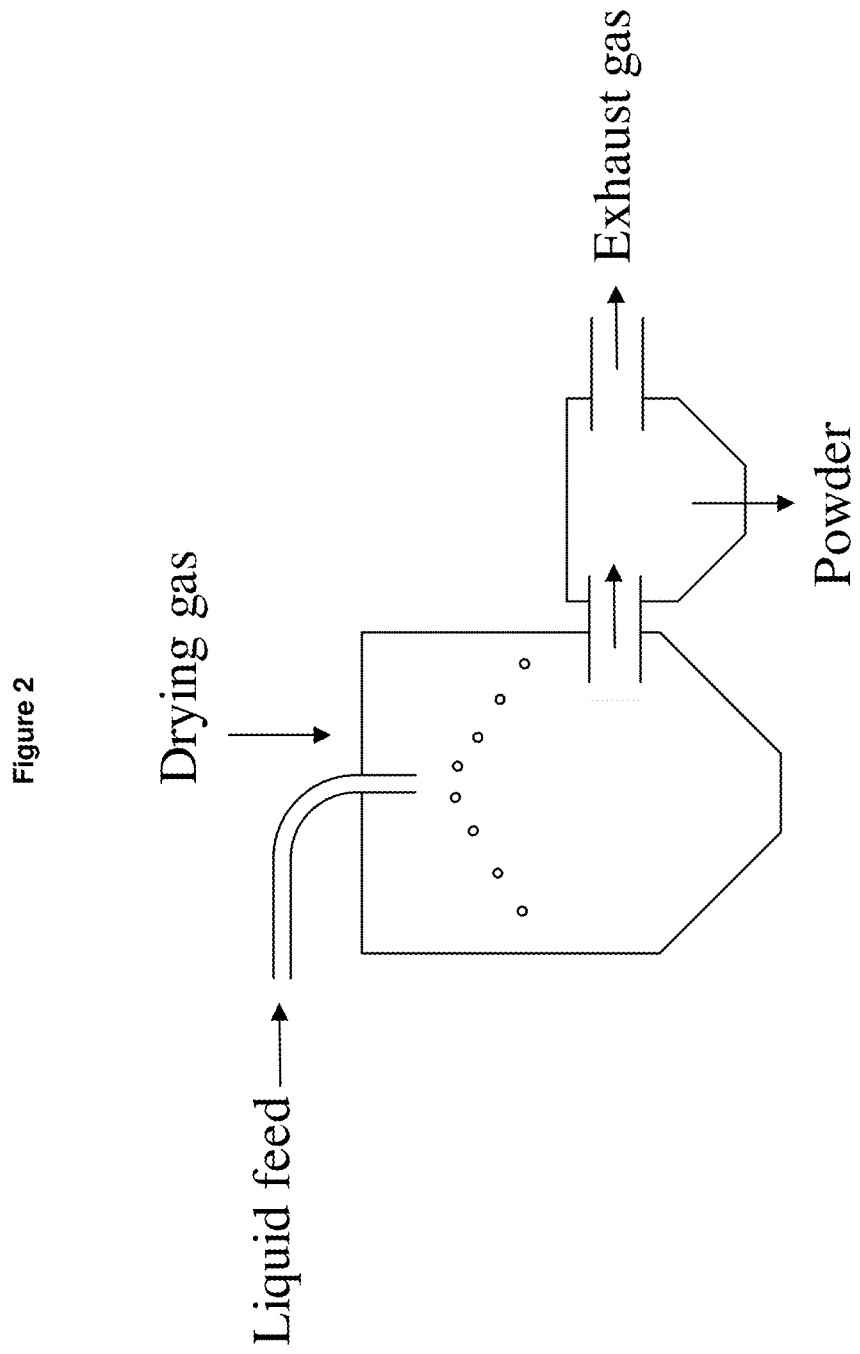
FIG. 2 is a schematic diagram of a part of an apparatus, which could be used in the spray drying process.

In certain embodiments, the invention is directed to the process of spray drying the liquid composition to obtain a dry composition. The basic steps of spray drying involve the production of fine droplets (e.g. atomization) by spraying the liquid to be dried through a nozzle and drying the fine droplets. Usually the drying of the fine droplets is accomplished by spraying said droplets into a heated gas stream. FIG. 2 provides a schematic representation of a spray drying apparatus using a heated gas stream.

In certain such embodiments, the temperature in the drying apparatus does not exceed 500° C., or 300° C., or 200° C. or about 140° C. In particular, the drying or contact temperature in step 2 does not exceed 500° C., or 300° C., or 200° C. or about 140° C. In certain embodiments, the temperature of the composition does not exceed 120° C. or 100° C. or 80° C.

In certain such embodiments, step 2 comprises the following sub-steps in accordance with a usual spray drying process:
sub-step 2.1: atomizing said liquid composition by spraying it through a nozzle to provide droplets in a drying chamber in a heated stream of gas,
sub-step 2.2: drying the droplets in the drying chamber in the heated stream of gas to form particles from the droplets, and
sub-step 2.3: recovering said particles from the drying chamber.

In certain such embodiments, sub-step 2.1 may involve using a flow of gas to force a liquid composition through a nozzle at a maximum feed rate of at least 4 mL/min in order to generate droplets and, wherein sub-step 2.2 may involve using a drying gas with a maximum flow rate of 25 kg/hour, or 10 kg/hour, or between 0.5 kg/hour and 5 kg/hour, or around 1.5 kg/hour.

In certain embodiments, sub-step 2.1. and 2.2 comprises exposing the composition to a stream of drying gas with a temperature of from about 80° C. to about 200° C., or from about 100° C. to about 150° C., or from about 120° C. to about 150° C.

In certain such embodiments, sub-step 2.3 comprises collecting the dry composition in a cyclone or filter.

According to the invention the log loss of activity (pfu/g) of at least one bacteriophage species from the liquid composition obtained in step 1 to the dried composition obtained in step 2 is less than about 2 ($10^2$), or less than about 1.5 ($10^{1.5}$) or less than about 1 ($10^1$). In certain embodiments the log loss of activity (pfu/g) of at least three bacteriophage species from the liquid composition in step 1 to the dried composition in step 2 is less than about 2 ($10^2$), or less than about 1.5 ($10^{1.5}$) or less than about 1.1 ($10^{1.1}$).

In certain embodiments, the percentage yield of dry composition obtained in step 2 based on the total weight of solid excipients added in step 1 is greater than 50%, or greater than 60%, or greater than 70%.

In certain embodiments, the dry bacteriophage composition is stable during storage at 25° C. and 60% relative humidity, with log loss of activity values after 1 month of less than about 2 to less than about 0.5. In certain embodiments, the dry bacteriophage composition demonstrates log loss of activity values after storage for 3 months of less than about 5 to less than about 0.8. In certain embodiments, the dry bacteriophage composition demonstrates log loss of activity values of the bacteriophage composition after 6 months of less than about 5 to less than about 1.

EXAMPLES

The following Examples are included to demonstrate certain aspects and embodiments of the invention as described in the claims. It should be appreciated by those of skill in the art, however, that the following description is illustrative only and should not be taken in any way as a restriction of the invention.

For the production of spray-dried bacteriophage compositions according to Examples 1-3 below the following materials were used:

Materials Used in the Compositions of Examples 1 to 3

| Material | Manufacturer/Supplier |
| --- | --- |
| Bulking agents | |
| Cleargum CO 03, batch E 247B | Roquette |
| Dextran 40 | AppliChem |
| Eudragit L 30 D-55 | Evonik |
| Eudragit L100 | Evonik |
| Hydroxyethyl starch (200/0.5) | Serumwerke Bernburg |
| Soluplus | BASF |
| Lyoprotectants | |
| Trehalose dihydrate | Merck, biochemical quality |
| Sorbitol | Merck |
| Sucrose | Merck |
| Buffer Substances | |
| Histidine | AppliChem |
| $NaH_2PO_4 \cdot 2H_2O$ | Merck |
| $K_2HPO_4$ | Merck |
| Hydrochloric acid (HCl) 0.5M | Merck |
| Sodium hydroxide solution 1M | Merck |
| Tris (Trometamol) | Merck |
| Buffered Sodium Chloride Peptone Solution (BSP) | Biomerieux |
| Polyethylene glycol (PEG6000) | Wako pure chemical |
| Glycerol | Wako pure chemical |
| NaCl | Wako pure chemical |
| L-Leucine | AppliChem |
| $MgSO_4 \cdot 7H_2O$ (magnesium sulfate hepta hydrate) | Merck |

-continued

| Material | Manufacturer/Supplier |
|---|---|
| Surfactants | |
| Polysorbate 20 | Merck |
| Poloxamer 188 | BASF |
| Solvents | |
| Water for injection, Ampuwa | Fresenius |
| Ethanol p.a. | Merck |
| Growth Medium | |
| Soybean casein digest (SCD) broth | Biomerieux |
| Agar | Biomerieux |
| Phages | |
| Escherichia coli bacteriophage T7 (NBRC20007) Accession number: NC_001604 | NITE Biological Resource Center (NBRC) |
| Pseudomonas aeruginosa bacteriophage M6 (NBRC20056) Accession number: NC_007809 | NITE Biological Resource Center (NBRC) |
| Staphylococcus aureus bacteriophage ΦSA012 (NBRC110650) Accession number: NC_023573 | NITE Biological Resource Center (NBRC) |
| Host Bacteria | |
| Escherichia coli (NBRC13168) | NITE Biological Resource Center (NBRC) |
| Pseudomonas aeruginosa (NBRC15483) | NITE Biological Resource Center (NBRC) |
| Staphylococcus aureus (NBRC110649) | NITE Biological Resource Center (NBRC) |
| Other materials | |
| Slide-A-Lyzer dialysis cassettes, 3 mL, 20 kDa | Thermo Scientific |
| PVDF membrane filter | Merck Millipore |
| XM-G agar | Nissui Pharmaceutical Co., Ltd |
| Enteric hard gelatin capsules (size 2) | Sunsho pharmaceutical, Shizuoka pref., Japan |
| Normal hard gelatin capsules (size 2) | Capsugel, Kanagawa-pref., Japan |

For the production of spray-dried compositions according to Examples 1-2 below the following stock solutions were used:

| Phages | Activity [pfu/mL] |
|---|---|
| Escherichia coli bacteriophage T7 (NBRC20007) | $7.8 \times 10^{11}$ |
| Pseudomonas aeruginosa bacteriophage M6 (NBRC20056) | $7.3 \times 10^{10}$ |

For the production of spray-dried compositions according to Example 3 below the following phage stock solutions were used:

| Phages | Activity [pfu/mL] |
|---|---|
| Escherichia coli bacteriophage T7 (NBRC20007) | $3.4 \times 10^{10}$ |
| Pseudomonas aeruginosa bacteriophage M6 (NBRC20056) | $2.2 \times 10^{10}$ |
| Staphylococcus aureus bacteriophage ΦSA012 (NBRC110650) | $6.1 \times 10^{10}$ |

Test Methods

Plaque assay: The activity of the phages was determined using a standard double-layer agar plate plaque assay. This involved inoculating host bacteria from the frozen stock into a 5 mL portion of SCD broth and incubating the resulting culture overnight at 32.5° C. with shaking. The culture was then passaged to a fresh 5 mL aliquot of SCD broth and incubated at 32.5° C. with shaking for about 3 hours. A 0.1 mL aliquot of this solution of the host bacteria was then mixed with a 0.1 mL aliquot of the sample being tested and 3 mL of melted SCD soft agar (a mixture of equal parts of SCD broth and SCD agar, with a 0.75% agar concentration). This was then immediately poured on to a SCD agar plate and allowed to solidify. The plate was then incubated at 32.5° C. overnight. The number of plaques formed on the plate were counted following overnight incubation. The total number of plaques was determined using the formula given below:

$$pfu = \frac{\text{Average number of plaques} \times \text{dilution factor}}{\text{Sample volume applied to plate (mL or gram)}}$$

Karl Fischer titration: The water content according to Examples 1-3 was measured using the Karl Fischer titration method using a Metrohm 851 Karl-Fischer-Coulometer equipped with a Metrohm 801 stirrer and a Metrohm Tiamo evaluation system. Approximately 100 mg of sample was weighed into an empty vial, which was then sealed immediately with an aluminium cap. The water in the sample was evaporated by heating the sample vessel in a Metrohm 874 Oven Sample Processor and the evaporated water was then transferred to the titration cell (oven temperature 120° C., nitrogen flow 40 mL/min). In the titration cell, the water consumes stoichiometric amounts of the titration reagent. The water content was determined by comparison of the amount of titration reagent consumed by the sample to that consumed by a blank sample (an empty vial).

Particles size measurement: The particle size according to Examples 1-3 was measured using a Malvern Mastersizer 2000 equipped with a Scirocco 2000 Module (for dry samples) using the following method:

(1) A small amount of the dry powder sample (5-10 mg) was placed in the sample receptor of the Scirocco module.
(2) A pressured difference was then used to blow the sample into the main Mastersizer module.
(3) In the Mastersizer the particles travel through a laser beam, which analyses the particle size distribution based on the principle of laser diffraction.
(4) Each sample was analysed two times (n=2) using a blue light ($\lambda$=470 nm) under 4 bar pressure. A refractive index of 1.400 was used to calculate the size of all samples, in order to allow comparison of the results, as the different compositions used for each example have different refractive indices.

Mean molecular weight ($M_w$) determinations: The mean molecular weight ($M_w$) may be determined using size exclusion chromatography, as detailed in the European Pharmacopoeia (European Pharmacopoeia (Ph. Eur.) $9^{th}$ Edition (9.0)), specifically for the excipients Dextran (section 2.2.39, pages 62-64) and HES (pages 3649-3652).

Section 2.2.39 of the European Pharmacopoeia (European Pharmacopoeia (Ph. Eur.) $9^{th}$ Edition (9.0)) specifies a method for determining the "molecular mass distribution in dextrans." This method may also be used for other $\alpha$-linked polymeric glucose molecules for which there is no monograph in the European Pharmacopoeia and hence no defined method for determining the $M_w$. Comparison of the retention volume of the sample of $\alpha$-linked polymeric glucose of interest and the retention volumes of the calibration standards produced using dextrans of known molecular weight (as specified in the European Pharmacopoeia (Ph. Eur.) $9^{th}$ Edition (9.0) and the List of European Pharmacopoeia Reference Standards, effective from 20018/2/5) means that the molecular weight of the $\alpha$-linked polymeric glucose may be estimated.

Size-exclusion chromatography is a chromatographic technique, which separates molecules in solution according to their size. This technique may be used to determine molecular masses by comparison with appropriate calibration standards (e.g. the calibration standards specified in the European Pharmacopoeia (Ph. Eur.) $9^{th}$ Edition (9.0)).

In general, the sample is introduced into a column, which is filled with a gel or a porous particle packing material, and is carried by the mobile phase through the column. The size separation takes place by repeated exchange of the solute molecules between the solvent of the mobile phase and the same solvent in the stationary phase within the pores of the packing material. The pore-size range of the packing material determines the molecular-size range within which separation can occur.

Molecules small enough to penetrate all the pore spaces elute at the total permeation volume ($V_t$). On the other hand, molecules larger than the maximum pore size of the packing material migrate along the column only through the spaces between the particles of the packing material without being retained and elute at the exclusion volume ($V_0$ void volume). Separation according to molecular size occurs between the exclusion volume and the total permeation volume, with useful separation usually occurring in the first two thirds of this range.

Apparatus: A chromatographic column of varying length and internal diameter is used.

The column is packed with a separation material, which is capable of fractionation in the appropriate range of molecular sizes and through which the mobile phase is passed at a constant rate. At one end of the column is a device for applying the sample e.g. a flow adapter, a syringe through a septum, an injector valve etc. The outlet of the column is usually connected to a suitable detector fitted with an automatic recorder, which enables monitoring of the relative concentrations of separated components in the sample. Detectors may be based e.g. on photometric, refractometric, luminescent etc. properties. The packing material may be soft (e.g. a swollen gel) or rigid (e.g. glass, silica or a solvent compatible, cross-linked organic polymer). The mobile phase is chosen according to the sample type, separation medium and method of detection. Before carrying out the separation, the column should be prepared appropriately (e.g. according to the manufacturer's instructions or according to the description in the European Pharmacopoeia (Ph. Eur.) $9^{th}$ Edition (9.0)).

Practically the molecular weight determination, in general involves the following steps:

A mobile phase is prepared, which may be e.g. a buffered solution.

A solution containing the carbohydrate sample of interest for which the $M_W$ is to be determined is prepared by dissolving the carbohydrate of interest in an aliquot of the mobile phase.

Calibration standards are prepared by dissolving reference substances (according to the List of European Pharmacopoeia Reference Standards, effective from 20018/2/5) in solution as specified in the European Pharmacopoeia (Ph. Eur.) $9^{th}$ Edition (9.0).

An appropriate column is then selected for carrying out the chromatographic procedure. For example for Dextrans a cross-linked agarose for chromatography R column may be used and for HES a hydroxylated polymethacrylate gel R column may be used.

An aliquot of solution containing the carbohydrate of interest should be added to the column or injected into the column.

A flow rate of approximately 0.5-1 mL/min may be used and detection may be carried out using a multiple-angle light scattering (MALS) detector and/or a (differential) refractometer maintained at a constant temperature.

Subsequently, aliquots of calibration standards should also be sequentially added to the column or injected into the column.

The retention volumes of the calibration standards may be plotted against the logarithm of their molecular masses. The plot usually approximates a straight line within the exclusion and total permeation limits for the separation medium used.

From the calibration curve, the mean molecular weight ($M_w$) of the carbohydrate sample of interest may be determined by comparison of the retention volume to those obtained with each of the calibration solutions.

Example 1

In Example 1, spray-dried drug compositions were prepared with the T7 bacteriophage drug substance. The processing steps in the manufacture of the spray-dried compositions were as follows:

1. Buffer Exchange Via Dialysis of Drug Substance

A dialysis step was carried out using a 3 mL Slide-A-Lyzer dialysis cassette with a 20 kDa cut off. The dialysis procedure was carried out as follows:
(1) The dialysis solution was prepared in a beaker. This solution had the same composition as the solution used in the spray drying process apart from the omission of large molecular weight excipients such as dextran 40, polysorbate, eudragit and hydroxyethyl starch.
(2) The Slide-A-Lyzer dialysis cassette was wetted in the dialysis solution.
(3) An aliquot of stock drug substance of about 2.5 g was injected into the sample cavity of the Slide-A-Lyzer cassette.
(4) The Slide-A-Lyzer cassette was placed into a vessel containing 500 g of dialysis solution.
(5) This solution was stirred overnight under ambient conditions to allow exchange of the buffer components.
(6) Following buffer exchange, the drug substance was removed from the sample cavity of the Slide-A-Lyzer and added to the spray drying solution.

2. Preparation of Solution

The process steps involved in the production of dispersions containing the bacteriophage active agent in Example 1 were as follows:
(1) For each Example and Comparative Example, all of the ingredients specified in Table 1(a), apart from the drug substance, were dissolved in 350 g to 400 g of water.
(2) The solution was then adjusted to the correct pH and stirred until a clear liquid was obtained.
(3) An aliquot of drug substance of about 2.5 g (following dialysis) was added and the solution was gently mixed, avoiding sheer stress.
(4) The solution was then diluted to a final weight of 500 g with water.
(5) The solution was spray-dried as described below.

3. Spray Drying of the Solution

The spray drying procedure in Example 1, was carried out using a GEA SD Micro spray dryer equipped with a two fluid nozzle with a 1 mm internal diameter. A flow rate of atomizing gas of 1.5 kg/h was used and a flow rate of nitrogen drying gas of 25 kg/h was used. The feed temperature was set at approximately 25° C., the product temperature at approximately 80° C. and the inlet temperature at approximately 137° C. The spray dying process was operated in a cascade mode with a feed rate of 5 mL/min. Following spray drying the powder was collected and the yield was determined.

The bacteriophage compositions in Examples 1.1 to 1.4 and Comparative Examples 1.5 to 1.8 were prepared following the procedures described above and the results after spray drying are shown in Table 1 (a).

The individual components of the mixture were added in the following concentrations: 5% w/w of solution of polyol and α-linked polymeric glucose (or Excipient 1 in the Comparative Examples), 20 mM Tris-HCl buffer, 20 mM histidine buffer, 20 mM phosphate buffer, 20 mM MgSO$_4$, 0.1% w/w of solution of leucine, 0.05% w/w of solution of polysorbate 20.

The activity of the liquid composition before spray drying for the Examples ranged from approximately $3 \times 10^9$ to approximately $5 \times 10^9$ pfu/mL. The activity following spray drying of the examples ranged from approximately $2 \times 10^7$ to approximately $2 \times 10^9$ pfu/g. The log loss of activity after spray drying was calculated on the basis of the exact weight of stock drug substance used for the individual experiment and the activity as stated in the table showing the theoretical activity based on the amount of drug substance used.

TABLE 1 (a)

| Examples | α-linked polymeric glucose (or Excipient 1) | Polyol | Weight ratio of α-linked polymeric glucose to Polyol | Buffer | pH | Surfactant | Particle size [μm] | Yield [g] | Yield [%] | Water content [%] | Log loss of activity |
|---|---|---|---|---|---|---|---|---|---|---|---|
| Example 1.1 | Dextran 40 (40 kDa) | — | — | Tris-HCl Leucine | 7.0 | — | 7.52 | 16.8 | 62.9 | 4.29 | 3.4 |
| Example 1.2 | Dextran 40 (40 kDa) | Sucrose | 8:2 | Tris-HCl Leucine | 7.0 | — | 6.47 | 15.36 | 57.5 | 2.83 | 2.1 |
| Example 1.3 | HES[a] (200 kDa) | — | — | Phosphate MgSO$_4$ | 7.0 | — | 8.41 | 17.8 | 64.2 | 3.69 | 2.1 |
| Example 1.4 | HES[a] (200 kDa) | Sucrose | 8:2 | Phosphate MgSO$_4$ | 7.0 | — | 7.25 | 16.3 | 58.5 | 2.72 | 1.7 |
| Comparative Example 1.5 | — | Trehalose | — | Histidine | 7.0 | — | 4.53 | 17.49 | 65.0 | 1.68 | 3.8 |
| Comparative Example 1.6 | — | Trehalose | — | Histidine | 7.0 | Polysorbate 20 | 4.9 | 11.78 | 43.3 | 1.79 | 4.6 |
| Comparative Example 1.7 | Eudragit[b] | — | — | Tris-HCl | 6.2 | — | 9.74 | 14.7 | 41.7 | 3.39 | 4.6 |
| Comparative Example 1.8[c] | SoluPlus | — | — | Tris-HCl | 7.0 | — | 7.22 | 13.4 | 50.1 | 0.76 | 4.2 |

[a]Hydroxyethyl starch (200/0.5),
[b]Eudragit L30 D-55 which contains 2.3% Polysorbate 80 and 0.7% SDS,
[c]Comparative Example 1.8 was prepared in a solution containing 50% v/v ethanol and spray-dried at a reduced temperature The results of stability tests for the spray-dried bacteriophage compositions in Example 1 after storage at 25° C. in 60% relative humidity for 1-6 months are given in Table 1 (b). The results in Table 1 (b) are displayed as log loss of activity ([pfu]/g) compared to the activity of the spray-dried compositions directly after spray drying. The log loss of activity for the liquid drug substance after storage at 25° C. in 60% relative humidity for 1-6 months compared to the activity of the liquid drug substance at the start of stability testing is also given in Table 1 (b) as a comparison.

TABLE 1 (b)

| Examples | α-linked polymeric glucose | Polyol | Weight ratio of α-linked polymeric glucose to Polyol | Log loss of activity [pfu/g] after: 1 Month | 3 Months | 6 Months |
|---|---|---|---|---|---|---|
| Liquid drug substance | — | — | — | 1.2 | 2.1 | 3.8 |
| 1.2 | Dextran | Sucrose | 8:2 | 0.5 | 0.8 | 1.0 |
| 1.3 | HES | — | — | 3.7 | 5.0 | 5.0 |
| 1.4 | HES | Sucrose | 8:2 | 0.9 | 1.8 | 2.9 |

Animal testing: capsules containing 100 mg of the spray-dried composition were administered to dogs in either normal or enteric-coated capsules. The dog faeces were sampled before and after administration. The number of plaques in the faeces was measured using a plaque assay as described above. This can then be used to calculate an activity per faeces sample. By summing the activity per sample over the time-period from 0-32 hours, it was possible to obtain a value for the total number of bacteriophage excreted and consequently to obtain a value for the percentage recovery of the bacteriophage following passage through the dog's gastrointestinal tract.

The results of an animal study carried out with the spray-dried composition in Example 1.2 (which contains dextran and sucrose in a ratio of 8:2) are shown in Table 1 (c):

TABLE 1 (c)

| Capsule | Theoretical dose [pfu/capsule] | Sampling point [hours] | Mass of faeces [g] | Activity [pfu/g] | Phage activity per sample [pfu] | Total number of bacteriophage excreted [pfu] | Recovery [%] |
|---|---|---|---|---|---|---|---|
| Normal | $9.8 \times 10^7$ | 0-4 | 71 | <50 | — | $3.1 \times 10^6$ | 3.2 |
| | | 8-24$^a$ | 8.7 | $3.5 \times 10^1$ | $3.0 \times 10^3$ | | |
| | | 8-24$^b$ | 134 | $2.3 \times 10^4$ | $3.1 \times 10^6$ | | |
| | | 28-32 | 64 | $5.0 \times 10^1$ | $3.2 \times 10^3$ | | |
| Enteric | $5.1 \times 10^7$ | 4-8 | 37 | <50 | — | $8.5 \times 10^6$ | 16.7 |
| | | 8-24$^a$ | 12 | $2.0 \times 10^2$ | $2.5 \times 10^3$ | | |
| | | 8-24$^b$ | 137 | $1.5 \times 10^2$ | $2.0 \times 10^4$ | | |
| | | 28-32 | 46 | $2.0 \times 10^5$ | $8.4 \times 10^6$ | | |

$^a$fresh faeces,
$^b$remaining faeces.

Example 2

The spray-dried compositions in Example 2 were prepared as described in Example 1 except that the M6 bacteriophage drug substance was used. The results after spray drying for these bacteriophage compositions are shown in Table 2 (a).

The individual components of the mixture were added in the following concentrations: 5% w/w of solution of polyol and α-linked polymeric glucose, 20 mM Tris-HCl, 20 mM phosphate buffer, 20 mM MgSO$_4$, 0.1% w/w of solution of Leucine.

The activity of the liquid composition before spray drying for the Examples ranged from approximately $2.5 \times 10^8$ to approximately $5 \times 10^8$ pfu/mL. The activity following spray drying of the Examples ranged from approximately $8 \times 10^6$ to approximately $4 \times 10^8$ pfu/g. The log loss of activity after spray drying was calculated on the basis of the exact weight of drug substance used for the individual experiment and the activity.

TABLE 2 (a)

| Example | α-linked polymeric glucose | Polyol | Weight ratio of α-linked polymeric glucose to Polyol | Buffer | pH | Particle size [μm] | Yield [g] | Yield [%] | Water content [%] | Log loss of activity |
|---|---|---|---|---|---|---|---|---|---|---|
| Example 2.1 | Dextran 40 (40 kDa) | Sucrose | 8:2 | Tris-HCl Leucine | 7.0 | 6.72 | 19.2 | 71.6 | 3.61 | 2.1 |
| Example 2.2 | Dextran 40 (40 kDa) | Sorbitol | 8:2 | Tris-HCl Leucine | 7.0 | 6.52 | 18.9 | 70.5 | 2.67 | 1.8 |
| Example 2.3[a] | Dextran 40 (40 kDa) | Sorbitol | 8:2 | Tris-HCl Leucine | 7.0 | 6.25 | 19.5 | 72.7 | 2.02 | 1.5 |
| Example 2.4 | HES[b] (200 kDa) | Sorbitol | 8:2 | Phosphate MgSO4 | 7.0 | 5.90 | 14.6 | 52.5 | 2.40 | 1.7 |
| Example 2.5 | HES[b] (200 kDa) | Sucrose | 8:2 | Phosphate MgSO4 | 7.0 | 6.49 | 16.2 | 58.5 | 3.22 | 1.5 |
| Example 2.6 | HES[b] (200 kDa) | Sucrose | 6:4 | Phosphate MgSO4 | 7.0 | 6.09 | 17.6 | 63.5 | 2.64 | 1.3 |

[a]Buffer exchange/dialysis step was not carried out with the drug substance in Example 2.3
[b]Hydroxyethyl starch (200/0.5).

The results of stability tests after storage of the spray-dried bacteriophage compositions in Example 2 at 25° C. in 60% relative humidity for a period of 1 to 3 months are given in Table 2 (b). The results in Table 2 (b) are displayed as log loss of activity ([pfu]/g) compared to the activity of the spray-dried formulations directly after spray drying. The log loss of activity for the liquid drug substance after storage at 25° C. in 60% relative humidity for a period of 1 to 3 months compared to the activity of the liquid drug substance at the start of stability testing is also given in Table 2 (b) for comparison.

TABLE 2 (b)

| Example | α-linked polymeric glucose | Polyol | Weight ratio of α-linked polymeric glucose to Polyol | Log loss of activity after [pfu/g]: 1 Month | 3 Months |
|---|---|---|---|---|---|
| Liquid drug substance | — | — | — | 0.2 | 1.4 |
| 2.1 | Dextran 40 | Sucrose | 8:2 | 0.1 | 1.0 |
| 2.3 | Dextran 40 | Sorbitol | 8:2 | 0.6 | 1.2 |
| 2.4 | HES | Sorbitol | 8:2 | 1.2 | 3.5 |
| 2.5 | HES | Sucrose | 8:2 | 0.8 | 2.0 |
| 2.6 | HES | Sucrose | 6:4 | 0.7 | 1.5 |

Example 3

In Example 3 spray-dried bacteriophage compositions containing mixtures of the bacteriophage species T7, M6 and φSA012 were prepared. The processing steps in the manufacture of the spray-dried compositions according to Example 3 were as follows:

1. Preparation of Solution (without Dialysis)

The process steps involved in the production of dispersions containing the bacteriophage active agent in Example 3 were as follows:

(1) For each Example and Comparative Example all of the components specified in Table 3(a), apart from the drug substance, were dissolved in 350 g to 400 g of water.

(2) The solution was then adjusted to the correct pH and stirred until a clear liquid was obtained.

(3) Three separate aliquots of drug substance for each species of bacteriophage, as specified in the table, of about 2.5 g were added and the solution was gently mixed, avoiding sheer stress. A buffer exchange step was not carried out with the drug substances in Example 3.

(4) The solution was then diluted to a final weight of 500 g with water.

(5) The solution was spray-dried as described below.

2. Spray Drying of Solution

The spray drying procedure in Example 3, was carried out as described in Example 1.

The spray-dried bacteriophage compositions in Example 3 were prepared following the procedures described above. The results after spray drying for these compositions are shown in Table 3 (a).

The individual components of the mixture were added in the following concentrations: 5% w/w of solution of polyol and α-linked polymeric glucose (or Excipient 1 in the Comparative Examples), 20 mM $MgSO_4$, 0.1% w/w leucine.

The activity of the liquid composition before spray drying for each of the bacteriophage per mL of solution was approximately $1\times10^8$ to approximately $3\times10^8$ pfu/mL for the T7 species, approximately $8\times10^7$ to approximately $2\times10^8$ pfu/mL for the M6 species and approximately $2\times10^8$ to approximately $4\times10^8$ pfu/mL for the φSA012 species.

The log loss of activity was calculated on the basis of the exact weight of drug substance used for the individual experiment and the activity as stated in the table showing theoretical activity based on the exact amount of drug substance used.

TABLE 3 (a)

| Example | α-linked polymeric glucose (or Excipient 1) | Polyol | Weight ratio of α-linked polymeric glucose (or Excipient 1) to Polyol | Buffer | pH | Electrolyte | Particle size [μm] | Yield [%] | Water content [%] | T7 Log loss of activity | M6 Log loss of activity | ΦSA012 Log loss of activity |
|---|---|---|---|---|---|---|---|---|---|---|---|---|
| Example 3.1 | Dextran 40 (40 kDa) | Sucrose | 4:6 | Tris-HCl 20 mM | 7.0 | Leucine | 6.03 | 74.4 | 2.77 | 1.0 | 1.2 | 1.3 |
| Example 3.2 | Dextran 40 (40 kDa) | Sucrose | 4:6 | Tris-HCl 5 mM | 7.0 | Leucine | 5.95 | 80.2 | 2.86 | 0.9 | 1.2 | 1.2 |
| Example 3.3 | HES[a](200 kDa) | Sucrose | 4:6 | Phosphate 20 mM | 7.0 | MgSO$_4$ | 5.25 | 63.6 | 3.52 | 1.4 | 1.4 | 1.5 |
| Example 3.4 | HES[a](200 kDa) | Sucrose | 4:6 | Tris-HCl 5 mM | 7.0 | Leucine | 5.51 | 70.6 | 2.14 | 0.7 | 1.0 | 1.0 |
| Comparative Example 3.5 | Eudragit L30D-55[b] | Sucrose | 8:2 | Tris-HCl 20 mM | 6.0 | — | 7.65 | 46.7 | 3.60 | 1.8 | 2.5 | 1.6 |
| Comparative Example 3.6 | Eudragit L100[c] | Sucrose | 8:2 | Tris-HCl 20 mM | 6.0 | — | 6.05 | 54.3 | 5.87 | 1.4 | 2.1 | 1.5 |

[a]Hydroxyethyl starch (200/0.5)
[b]Eudragit L30 D-55 which contains 2.3% Polysorbate 80 and 0.7% SDS
[c]Eudragit L100 contains 0.3% SDS.

Further Items of the Invention

The invention relates in particular to the following further items:

1. A bacteriophage composition comprising:
   at least one bacteriophage species, and
   at least one α-linked polymeric glucose
   at least one polyol,
   and optionally other ingredients selected from the group of buffer salts, electrolytes and surfactants.
2. The bacteriophage composition according to item 1, wherein the α-linked polymeric glucose has a mean molecular weight of at least about 5 kDa.
3. The bacteriophage composition according to item 1, wherein the α-linked polymeric glucose has a mean molecular weight of at least about 10 kDa.
4. The bacteriophage composition according to item 1, wherein the α-linked polymeric glucose has a mean molecular weight of at least about 30 kDa.
5. The bacteriophage composition according to item 1, wherein the α-linked polymeric glucose has a mean molecular weight of at least about 40 kDa.
6. The bacteriophage composition according to item 1, wherein the α-linked polymeric glucose has a mean molecular weight of at least about 100 kDa.
7. The bacteriophage composition according to item 1, wherein the α-linked polymeric glucose has a mean molecular weight of at least about 150 kDa.
8. The bacteriophage composition according to item 1, wherein the α-linked polymeric glucose has a mean molecular weight of at least about 200 kDa.
9. The bacteriophage composition according to any one of items 1 to 8, further comprising at least one buffer system.
10. The bacteriophage composition of any one of items 1 to 9, further comprising at least one electrolyte.
11. The bacteriophage composition of any one of items 1 to 10, comprising at least two different bacteriophage species.
12. The bacteriophage composition according to item 11, comprising at least three different bacteriophage species.
13. The bacteriophage composition according to any one of items 1 to 12, wherein one or more of the bacteriophage species are selected from the group of Caudovirales.
14. The bacteriophage composition according to item 13, wherein one or more of the bacteriophage species are selected from the subgroups of Myoviridae, Podoviridae, Siphoviridae or mixtures thereof.
15. The bacteriophage composition according to any one of items 1 to 14, wherein at least one of the bacteriophage species has a prolate shaped head.
16. The bacteriophage composition according to any one of items 1 to 15, wherein at least one of the bacteriophage species has an isometric shaped head.
17. The bacteriophage composition according to any one of items 1 to 16, wherein at least one of the bacteriophage species is effective against gram-positive bacteria.
18. The bacteriophage composition according to any one of items 1 to 17, wherein at least one of the bacteriophage species is effective against gram-negative bacteria.
19. The bacteriophage composition according to any one of items 1 to 18, wherein at least one of the bacteriophage species is effective against at least one of the bacterial organisms selected from the group of *Escherichia coli*, *Pseudomonas aeruginosa* and *Staphylococcus aureus*.
20. The bacteriophage composition according to any one of items 1 to 19, wherein the α-linked polymeric glucose is selected from dextrans and starches including modified starches.
21. The bacteriophage composition according to item 20, wherein the α-linked polymeric glucose is a starch.
22. The bacteriophage composition according to item 20, wherein the α-linked polymeric glucose is a modified starch.
23. The bacteriophage composition according to item 20, wherein the α-linked polymeric glucose is a hydroxyalkyl starch, such as hydroxyethyl starch.
24. The bacteriophage composition according to item 20, wherein the α-linked polymeric glucose is a dextran.
25. The bacteriophage composition according to any one of items 1 to 24, wherein the polyol is a disaccharide.

26. The bacteriophage composition according to item 25, wherein the polyol is sucrose.

27. The bacteriophage composition according to item 26, wherein the α-linked polymeric glucose is hydroxyethyl starch.

28. The bacteriophage composition according to any one of items 1 to 24,
wherein the polyol is sorbitol.

29. The bacteriophage composition according to any one of items 1 to 28,
wherein the weight ratio of α-linked polymeric glucose to the polyol is from about 9:1 to about 1:9.

30. The bacteriophage composition according to item 29, wherein the weight ratio of α-linked polymeric glucose to the polyol is from about 9:2 to about 1:9.

31. The bacteriophage composition according to item 30, wherein the weight ratio α-linked polymeric glucose to the polyol is from about 6:2 to about 2:8.

32. The bacteriophage composition according to item 31, wherein the weight ratio of α-linked polymeric glucose to the polyol is about 4:6.

33. The bacteriophage composition according to any of the preceding items in the form of a liquid composition.

34. The bacteriophage composition according to item 33 in the form of an aqueous composition.

35. The bacteriophage composition according to items 33 or 34,
wherein the pH is from about 6 to about 9, such as about 7.

36. The bacteriophage composition according to items 33 to 35,
wherein the activity of at least one bacteriophage species is from about $1\times10^7$ (pfu/mL) to about $1\times10^{25}$ (pfu/mL).

37. The bacteriophage composition according to item 36, wherein the activity of at least three bacteriophage species of is from about $1\times10^7$ (pfu/mL) to about $1\times10^{25}$ (pfu/mL).

38. The bacteriophage composition according to any one of items 33 to 37,
wherein the total mass of α-linked polymeric glucose comprises from about 2% w/w to 20% w/w, of the total weight of the liquid composition, or from about 2% w/w to 10% w/w, or from about 2% w/w to 8% w/w.

39. The bacteriophage composition according to items 33 or 34, which comprises
from about 3 mM to 10 mM Tris-HCl
from about 1% w/w to about 3% w/w of the liquid composition of hydroxyethyl starch
from about 2% w/w to about 4% w/w of the liquid composition of sucrose
from about 0.05% w/w to about 0.2% w/w of the liquid composition of leucine, and
wherein the composition
has a pH of about 7.0, and
wherein all the bacteriophage species have an activity of $1\times10^7$ (pfu/mL) to $1\times10^{20}$ (pfu/mL).

40. The bacteriophage composition according to any one of items 1 to 32 in the form of a dry composition and wherein the water content is less than 10% w/w, or less than 8% w/w, or less than 5% w/w, or less than 4% w/w.

41. The bacteriophage composition of item 40, wherein, the average diameters of the dry particles are between 3 μm and 150 μm.

42. A dry bacteriophage composition obtainable by spray drying a liquid composition according to any one of items 33 to 39.

43. A dry bacteriophage composition obtainable by lyophilization of a liquid composition according to any one of items 33 to 39.

44. The dry bacteriophage composition according to items 40 to 43,
wherein the activity of at least one of the bacteriophage species is at least $1\times10^6$ (pfu/g) and optionally up to a maximum of $1\times10^{25}$ (pfu/g) per gram of dried composition, preferably at least $1\times10^8$ (pfu/g) and optionally up to a maximum of $1\times10^{25}$ (pfu/g) per gram of dried composition or more preferably at least $1\times10^9$ (pfu/g) and optionally up to a maximum of $1\times10^{20}$ (pfu/g) per gram of dried composition.

45. The dry bacteriophage composition according to any one of items 40 to 44 provided in a capsule.

46. The dry bacteriophage composition according to item 45,
wherein the capsule is an enteric capsule.

47. The dry bacteriophage composition according to any one of items 40 to 44 in the form of a tablet.

48. The dry bacteriophage composition according to item 47 provided in the form of an enteric tablet, such as an enterically coated tablet.

49. A method of treating a bacterial infection comprising administering to an animal or human patient in need of such a treatment a unit dose of the dry bacteriophage composition according to any one of items 40 to 48.

50. Use of a bacteriophage composition according to any one of items 1 to 48 in the manufacture of a medicament for the treatment of a bacterial infection.

51. A unit dose of a dry bacteriophage composition according to item 50 for use in the treatment of a bacterial infection.

52. Dry bacteriophage compositions according to any one of items 40 to 48 for use in the treatment of a bacterial infection.

53. Use of an α-linked polymeric glucose and a polyol for the stabilization of bacteriophage species during spray drying.

54. The use of item 53,
wherein the α-linked polymeric glucose has a mean molecular weight of at least about 5 kDa.

55. The use of item 53,
wherein the α-linked polymeric glucose has a mean molecular weight of at least about 10 kDa.

56. The use of item 53,
wherein the α-linked polymeric glucose has a mean molecular weight of at least about 30 kDa.

57. The use of item 53,
wherein the α-linked polymeric glucose has a mean molecular weight of at least about 40 kDa.

58. The use of item 53,
wherein the α-linked polymeric glucose has a mean molecular weight of at least about 100 kDa.

59. The use of item 53,
wherein the α-linked polymeric glucose has a mean molecular weight of at least about 150 kDa.

60. The use of item 53,
wherein the α-linked polymeric glucose has a mean molecular weight of at least about 200 kDa.

61. The use of any one of items 53 to 60,
wherein the α-linked polymeric glucose, is a starch.

62. The use of any one of items 53 to 61,
wherein the α-linked polymeric glucose, is a modified starch.

63. The use of any one of items 53 to 62,
wherein the α-linked polymeric glucose, is a hydroxyethyl starch.
64. The use of any one of items 53 to 60,
wherein the α-linked polymeric glucose is dextran.
65. The use of any one of items 53 to 64,
wherein the polyol is sucrose.
66. The process of preparing a dried bacteriophage composition comprising at least step 1 and step 2, involving
preparing in step 1 a composition in an evaporable liquid comprising:
at least one bacteriophage species,
at least one α-linked polymeric glucose,
at least one polyol,
and optionally other ingredients selected from the group of buffer salts, electrolytes, surfactants, and
spray drying said liquid composition from step 1 in step 2 to obtain a dry bacteriophage composition.
67. The process of preparing a dried bacteriophage composition according to item 66,
wherein the α-linked polymeric glucose has a mean molecular weight of at least about 5 kDa.
68. The process of preparing a dried bacteriophage composition according to item 66,
wherein the α-linked polymeric glucose has a mean molecular weight of at least about 10 kDa.
69. The process of preparing a dried bacteriophage composition according to item 66,
wherein the α-linked polymeric glucose has a mean molecular weight of at least about 30 kDa.
70. The process of preparing a dried bacteriophage composition according to item 66,
wherein the α-linked polymeric glucose has a mean molecular weight of at least about 40 kDa.
71. The process of preparing a dried bacteriophage composition according to item 66,
wherein the α-linked polymeric glucose has a mean molecular weight of at least about 100 kDa.
72. The process of preparing a dried bacteriophage composition according to item 66,
wherein the α-linked polymeric glucose has a mean molecular weight of at least about 150 kDa.
73. The process of preparing a dried bacteriophage composition according to item 66,
wherein the α-linked polymeric glucose has a mean molecular weight of at least about 200 kDa.
74. The process according to any one of items 66 to 73,
wherein in step 2 the drying is carried out in a drying apparatus and wherein the temperature in the drying apparatus in step 2 does not exceed 500° C., or 300° C., or 200° C. or 140° C.
75. The process according to item 74,
wherein the contact temperature does not exceed 500° C., or 300° C., or 200° C. or 140° C.
76. The process according to items 66 to 75,
wherein step 2 comprises the following sub-steps:
sub-step 2.1: atomizing said liquid composition by spraying it through a nozzle to provide droplets in a drying chamber in a heated stream of gas,
sub-step 2.2: drying the droplets in the drying chamber in the heated stream of gas to form particles from the droplets, and
sub-step 2.3: recovering said particles from the drying chamber.
77. The process of item 76,
wherein sub-step 2.1 involves using a flow of gas to force a liquid composition through a nozzle at a feed rate of at least 4 mL/min in order to generate droplets and, wherein sub-step 2.2 involves using a drying gas with a flow rate of at least 25 kg/hour.
78. The process of items 75 or 76,
wherein sub-step 2.2 comprises exposing the composition to a stream of drying gas with a temperature of from about 80° C. to about 200° C., or from about 100° C. to about 150° C., or from about 120° C. to about 150° C.
79. The process of any one of items 76 to 78,
wherein sub-step 2.3 comprises collecting the dry particles in a cyclone or filter.
80. The process of any one of items 66 to 79,
wherein the log loss of activity (pfu/g) of at least one bacteriophage species from the liquid composition obtained in step 1 to the dried composition obtained in step 2 is less than 2, or less than 1.5, or less than 1.
81. The process of any one of items 66 to 80,
wherein the log loss of activity (pfu/g) of at least three bacteriophage species from the liquid composition in step 1 to the dried composition in step 2 is less than 2, or less than 1.5 or less than 1.1.
82. The process of any one of items 66 to 81,
wherein the yield of dry composition obtained in step 2 based on the total weight of solid excipients added in step 1 is greater than 50%, or greater than 60%, or greater than 70%.
83. The process of any one of items 66 to 82,
wherein the α-linked polyglucose is a starch.
84. The process of any one of items 66 to 83,
wherein the α-linked polyglucose is a modified starch.
85. The process of item 84,
wherein the α-linked polyglucose is a hydroxyalkyl starch, such as hydroxyethyl starch.
86. The process of items 66 to 82,
wherein the α-linked polyglucose is a dextran.
87. A spray dried bacteriophage composition according to any one of items 1 to 32.
88. A kit comprising the following components:
a) at least one unit dose of the spray dried bacteriophage composition according to item 87,
b) optionally a pharmaceutically acceptable liquid such as sterile water or a sterile buffer for reconstitution, and.
c) optionally at least one syringe suitable for injecting the composition.
89. A method of treating a bacterial infection comprising administering to an animal or human patient in need of such a treatment a unit dose of a spray dried bacteriophage composition according to item 87.
90. The method of item 89, wherein the unit dose of the spray dried bacteriophage composition is reconstituted in a pharmaceutically acceptable liquid such as sterile water or a sterile buffer for reconstitution.
91. The method of item 90, wherein the reconstituted unit dose is administered by injection.

The invention claimed is:
1. A bacteriophage composition comprising:
at least one bacteriophage species,
at least one α-linked polymeric glucose,
at least one polyol, wherein the polyol is sucrose or sorbitol,
and optionally other ingredients selected from the group of buffer salts, electrolytes and surfactants, and wherein the weight ratio of the α-linked polymeric glucose to the polyol is about 4:6 to 8:2.

2. The bacteriophage composition according to claim 1, wherein the α-linked polymeric glucose has a mean molecular weight from about 10 kDa to 1000 kDa, or from about 30 kDa to about 1000 kDa, or from about 150 kDa to about 800 kDa.

3. The bacteriophage composition according to claim 1 in the form of a dry composition, wherein the water content is less than 10% w/w, or less than 8% w/w, or less than 5% w/w, or less than 4% w/w.

4. A dry bacteriophage composition according to claim 3, obtainable by spray drying a liquid composition.

5. The bacteriophage composition according to claim 1, wherein one or more of the bacteriophage species are selected from the group of Caudovirales.

6. The bacteriophage composition according to claim 1, wherein the α-linked polymeric glucose is selected from the group of dextrans and starches.

7. The bacteriophage composition according to claim 6, wherein the α-linked polymeric glucose is a modified starch.

8. The bacteriophage composition according to claim 6, wherein the α-linked polymeric glucose is a dextran.

9. A method of treating a bacterial infection comprising
administering to an animal or human patient in need of such a treatment a unit dose of the dry bacteriophage composition according to claim 3, or
administering to an animal or human patient in need of such a treatment a unit dose of a reconstituted liquid bacteriophage composition obtainable by reconstituting the dry composition according to claim 3 in a pharmaceutically acceptable liquid.

10. A method for stabilizing a bacteriophage species during spray drying, the method comprising spray drying a bacteriophage species in combination with an α-linked polymeric glucose with a mean molecular weight of from about 10 kDa to about 1000 kDa, and a polyol, wherein the polyol is sucrose or sorbitol, and wherein the weight ratio of the α-linked polymeric glucose to the polyol is about 4:6 to 8:2.

11. The method of claim 10, wherein the α-linked polymeric glucose is a hydroxyethyl starch or a dextran.

12. A process of preparing a dried bacteriophage composition comprising at least step 1 and step 2, involving preparing in step 1 a composition in an evaporable liquid comprising:

at least one bacteriophage species,
at least one α-linked polymeric glucose,
at least one polyol, wherein the polyol is sucrose or sorbitol,
and optionally other ingredients selected from buffer salts, electrolytes and surfactants, wherein the weight ratio of the α-linked polymeric glucose to the polyol is about 4:6 to 8:2, and
spray drying said liquid composition from step 1 in step 2 to obtain a dry bacteriophage composition.

13. The process according to claim 12, wherein the α-linked polymeric glucose has a mean molecular weight of from about 10 kDa to about 1000 kDa or from about 40 kDa to about 1000 kDa, or from about 150 kDa to about 1000 kDa.

14. The process of claim 12, wherein the log loss of activity (pfu/g) of at least three bacteriophage species from the liquid composition in step 1 to the dried particles in step 2 is less than 2, or less than 1.5 or less than 1.1.

15. The bacteriophage composition according to claim 5, wherein one or more of the bacteriophage species are selected from the subgroups of Myoviridae, Podoviridae, Siphoviridae or mixtures thereof.

16. The bacteriophage composition according to claim 7, wherein the α-linked polymeric glucose is a hydroxyalkyl starch.

17. The bacteriophage composition according to claim 16, wherein the α-linked polymeric glucose is a hydroxyethyl starch.

18. The method of claim 10, wherein the α-linked polymeric glucose has a mean molecular weight of from about 40 kDa to about 1000 kDa.

19. The method of claim 10, wherein the α-linked polymeric glucose has a mean molecular weight of from about 150 kDa to about 1000 kDa.

20. The bacteriophage composition according to claim 3, wherein the composition maintains stable activity of the bacteriophage species during storage at 25° C. and 60% relative humidity over 1 month characterized by a log loss of activity of less than about 2 to less than about 0.5 pfu/g, over 3 months characterized by a log loss of activity of less than about 5 to less than about 0.8 pfu/g, or over 6 months characterized by a log loss of activity of less than about 5 to less than about 1.

* * * * *

UNITED STATES PATENT AND TRADEMARK OFFICE
CERTIFICATE OF CORRECTION

Page 1 of 1

PATENT NO. : 12,337,020 B2
APPLICATION NO. : 17/047611
DATED : June 24, 2025
INVENTOR(S) : Markus Rast, Sergio Rodriguez-Morillas and Tomomine Iida It is certified that error appears in the above-identified patent and that said Letters Patent is hereby corrected as shown below:

On the Title Page

Item (71) Applicants, please remove the Applicant "TAKEDA GMBH, Constance (DE)".

Signed and Sealed this
Twelfth Day of August, 2025

Coke Morgan Stewart
*Acting Director of the United States Patent and Trademark Office*